United States Patent [19]

Ohashi et al.

[11] Patent Number: 5,801,258
[45] Date of Patent: Sep. 1, 1998

[54] AMIDE DERIVATIVES AND DERMATOLOGIC PREPARATIONS CONTAINING THE SAME

[75] Inventors: Yukihiro Ohashi; Akira Kawamata; Yukihiro Yada; Kazuhiko Higuchi; Kazue Tsukahara; Genji Imokawa, all of Tochigi, Japan

[73] Assignee: Kao Corporation, Tokyo, Japan

[21] Appl. No.: 841,788

[22] Filed: May 5, 1997

Related U.S. Application Data

[62] Division of Ser. No. 256,344, filed as PCT/JP93/01676, Nov. 16, 1993, Pat. No. 5,659,052.

[30] Foreign Application Priority Data

Nov. 20, 1992 [JP] Japan ................... 4-312418
Aug. 31, 1993 [JP] Japan ................... 5-216484

[51] Int. Cl.[6] .................. C07D 317/18; C07D 317/28
[52] U.S. Cl. .................. 549/448; 549/452; 549/453; 549/454
[58] Field of Search .................. 549/448, 452, 549/453, 454

[56] References Cited

U.S. PATENT DOCUMENTS

| | | | |
|---|---|---|---|
| 5,175,321 | 12/1992 | Ohashi et al. | 554/63 |
| 5,208,355 | 5/1993 | Scott | 554/37 |

FOREIGN PATENT DOCUMENTS

| | | |
|---|---|---|
| 0398272 | 11/1990 | European Pat. Off. |
| 0455429 | 11/1991 | European Pat. Off. |
| 0495624 | 7/1992 | European Pat. Off. |
| 4-225907 | 8/1992 | Japan |
| 7-002698 | 1/1995 | Japan |

*Primary Examiner*—Ba K. Trinh
*Attorney, Agent, or Firm*—Birch, Stewart, Kolasch & Birch, LLP

[57] ABSTRACT

The amide derivative of the present invention is one represented by the following general formula (I) and the dermatologic preparation of the present invention is one containing said amide derivative.

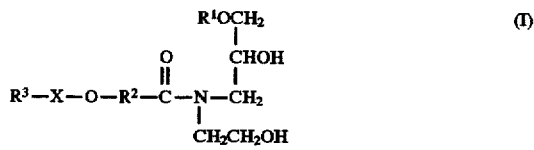

wherein $R^1$ represents a straight-chain or branched, saturated or unsaturated hydrocarbon group carrying 10 to 40 carbon atoms; $R^2$ represents a straight-chain or branched, saturated or unsaturated hydrocarbon group carrying 3 to 39 carbon atoms; $R^3$ represents a group containing at least one group represented by the formula:

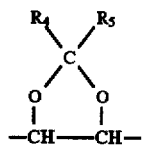

wherein $R^4$ and $R^5$ each represents a hydrogen atom or a straight-chain or branched or cyclic, saturated or unsaturated hydrocarbon group, or $R^4$ and $R^5$ may form a hydrocarbon group together; and X represents

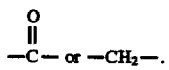

1 Claim, No Drawings

AMIDE DERIVATIVES AND DERMATOLOGIC PREPARATIONS CONTAINING THE SAME

This application is a divisional of application Ser. No. 08/256,344, filed on Jul. 13, 1994, now U.S. Pat. No. 5,659,052, which is a 371 application of PCT/JP93/01676 dated Nov. 16, 1993, the entire contents of which are hereby incorporated by reference.

BACKGROUND OF THE INVENTION

1. [Field of the Invention]

This invention relates to novel amide derivatives and dermatologic preparations containing the same. More particularly, it relates to dermatologic preparations capable of fundamentally improving the barrier functions of the horny layer, namely, exerting effects of maintaining normal barrier functions and restoring damaged barrier functions.

2. [Description of the Prior Art]

The skin, in particular, the horny layer is an extremely thin epidermic constituent which is located on the outermost side of the body. It not only protects the body from external irritation and invasion of foreign substances but also inhibits the loss and evaporation of the constituents and moisture contained in the body. Those protecting effects, i.e., the barrier functions of the horny layer are important in controlling the homeostasis in the physiological functions of the skin.

When these barrier functions of the horny layer are weakened by some internal or external reasons, for example, the skin frequently suffers from troubles such as inflammation, chapping or the acceleration of aging. Therefore, it is needless to say that the maintenance and reinforcement of the barrier functions of the horny layer are highly important for the skin and, in its turn, for our healthy daily life.

To prevent the occurrence of these skin troubles or to remedy the same, there have been employed dermatologic preparations containing various natural and synthetic ingredients. However, most of these dermatologic preparations aim at humidifying the skin and making up for the barrier functions by forming a coating on the surface of the skin. Namely, these dermatologic preparations merely make up for the barrier functions of the skin by forming a tentative coating on the surface of the skin. Thus they cannot be expected too much in the effects of essentially improving (maintaining and restoring) the barrier functions.

Thus, the present applicant has formerly proposed dermatologic preparations containing amide derivatives represented by the following general formula as dermatologic preparations capable of essentially improving the barrier functions of the skin (see Japanese Patent Laid-Open No. 306952/1990). Further, Scott et al. have proposed cosmetic compositions containing amide derivatives of similar structures (see Japanese Patent Laid-Open No. 225907/1992). Although these amide derivatives act on the horny layer and thus exert effects of essentially improving the barrier functions of the skin, the application of them to dermatologic preparations still involves some problems relating to the solubility in bases and oxidation stability.

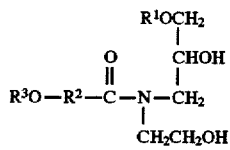

(wherein $R^1$ represents a straight-chain or branched, saturated or unsaturated hydrocarbon group carrying 10 to 40 carbon atoms; $R^2$ represents a straight-chain or branched hydrocarbon group carrying 3 to 39 carbon atoms; and $R^3$ represents a hydrogen atoms, a straight-chain or branched, saturated or unsaturated hydrocarbon group carrying 10 to 40 carbon atoms or an acyl group).

SUMMARY OF THE INVENTION

Accordingly, it is an object of the present invention to provide a compound which has effects of fundamentally improving (maintaining and reinforcing) the barrier functions of the horny layer, has a high solubility in a base and an excellent oxidation stability when blended in a dermatologic preparation, and thus can be stably and easily blended in a base, and a dermatologic preparation containing the above-mentioned compound which improves the barrier functions of the horny layer and prevents chapping, inflammation and aging of the skin when applied to the skin.

The present inventors have conducted extensive studies and, as a result, found out that the above-mentioned object of the present invention can be achieved by a novel amide derivative represented by the following general formula (I) or (II) and a dermatologic preparation containing said amide derivative, thus completing the present invention:

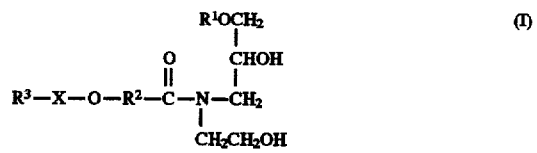

(I)

(wherein $R^1$ represents a straight-chain or branched, saturated or unsaturated hydrocarbon group carrying 10 to 40 carbon atoms; $R^2$ represents a straight-chain or branched, saturated or unsaturated hydrocarbon group carrying 3 to 39 carbon atoms; and $R^3$ represents a group containing at least one group represented by the formula:

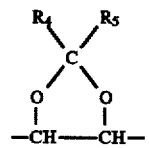

(wherein $R^4$ and $R^5$ each represents a hydrogen atom or a straight-chain, branched or cyclic, saturated or unsaturated hydrocarbon group, or $R^4$ and $R^5$ may form a hydrocarbon group together; and X represents

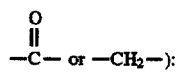

-continued

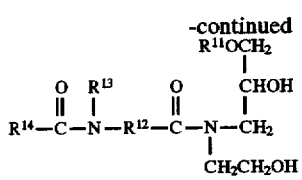
(II)

(wherein $R^{11}$ represents a straight-chain or branched hydrocarbon group carrying 10 to 40 carbon atoms; $R^{12}$ represents a straight-chain or branched hydrocarbon group carrying 1 to 39 carbon atoms; $R^{13}$ represents a hydrogen atom or a hydrocarbon group carrying 1 to 6 carbon atoms; and $R^{14}$ represents a hydrogen atom or a hydrocarbon group having a straight-chain, branched or cyclic structure and carrying 1 to 40 carbon atoms which may contain an oxygen atom).

Accordingly, the present invention provides an amide derivative represented by the above general formula (I) or (II) and a dermatologic preparation containing the same.

The amide derivative according to the present invention has effects of essentially improving (maintaining and reinforcing) the barrier functions of the horny layer. When blended in a dermatologic preparation, it shows a high solubility in a base and an excellent oxidation stability and, therefore, can be stably and easily blended in a base. When applied to the skin, the dermatologic preparation containing the amide derivative of the present invention essentially improves the barrier functions of the horny layer. Thus it is expected to be effective in remedying or preventing skin inflammation and chapping.

DETAILED DESCRIPTION OF THE INVENTION

First, the amide derivative represented by the above general formula (I) according to the present invention will be described in detail.

In the amide derivative of the present invention represented by the above general formula (I), particular examples of the hydrocarbon group represented by $R^1$ in the general formula (I) include decyl, dodecyl, tetradecyl, hexadecyl, octadecyl, docosyl, dotriacontyl, methyl-branched isostearyl, 2-ethylhexyl, 2-heptylundecyl, 9-octadecenyl and cholesteryl groups. Particular examples of the hydrocarbon group represented by $R^2$ include trimethylene, tetramethylene, octamethylene, decamethylene, undecamethylene, tetradecamethylene, pentadecamethylene, nonacontamethylene, octane-1,3-diyl, decane-1,3-diyl, heptadecane-1,11-diyl and 8-heptadecene-1,11-diyl groups.

As the hydrocarbon groups represented by $R^4$ and $R^5$ in the group represented by the following [Formula 1] contained in the group represented by $R^3$, those having 1 to 8 carbon atoms are preferable. Particular examples of the group represented by the following [Formula 1] include those represented by the following [Formula 2]:

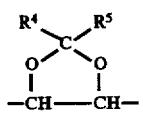
[Formula 1]

(wherein $R^4$ and $R^5$ are as defined above).

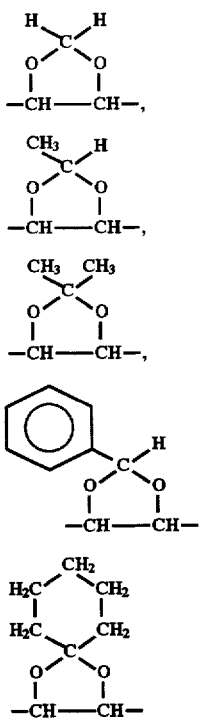
[Formula 2]

As the group represented by $R^3$, straight-chain or branched, saturated or unsaturated hydrocarbon groups wherein a carbon—carbon bond in the main chain is substituted with a group represented by the above [Formula 1] are preferable and those carrying 3 to 40 carbon atoms, excluding the carbon atoms in $R^4$ and $R^5$, are still preferable. In the group represented by $R^3$, the groups represented by the above [Formula 1] may be located either consecutively or with a hydrocarbon group interposed between them. Particular examples of the group represented by $R^3$ containing the group represented by the above [Formula 1] includes those represented by the following [Formula 3]:

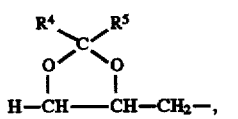
[Formula 3]

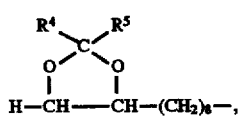

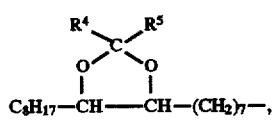

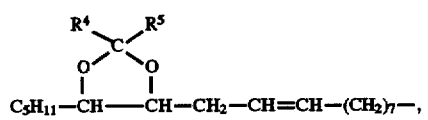

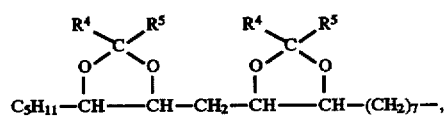

-continued

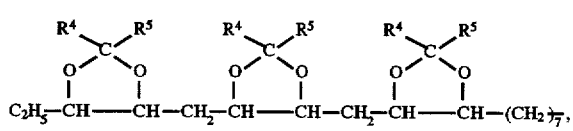

(wherein $R^4$ and $R^5$ are as defined above).

dehydrating agent (for example, one represented by the following [Formula 6]) or derived into an acid chloride (VIII) and treated with a base to thereby give an amide derivative (IX). Finally, the protecting groups $R^8$ are eliminated (when they are acetyl groups, a base such as $K_2CO_3$ or $Na_2CO_3$ is used in a lower alcohol, and when they are tert-butyldiphenylsilyl groups, a fluoride ion such as tetrabutylammonium fluoride is used) to thereby give the aimed amide derivative (I-A).

[Formula 4]

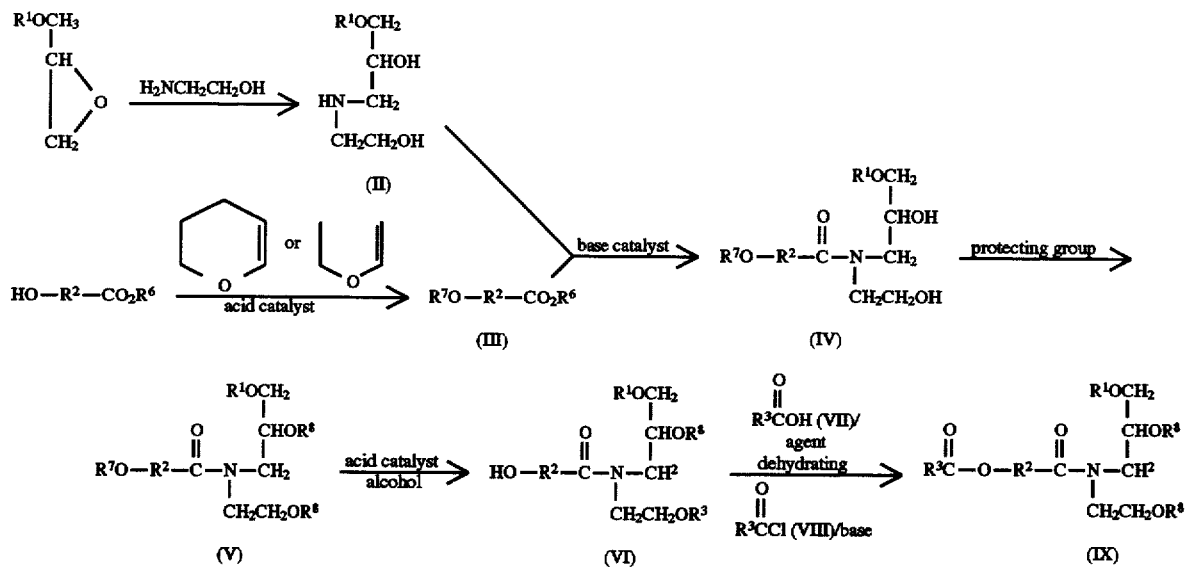

[Formula 5]

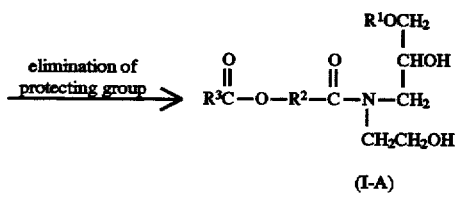

Methods for preparing the amide derivative of the present invention represented by the above general formula (I) are not particularly restricted. For example, it can be prepared by the following methods (1) and (2) in accordance with the method described in Japanese Patent Laid-Open No. 306952/1990.

(1) Method for preparing an amide derivative (I-A) of the above-mentioned general formula (I) wherein X is —CO—:

According to the reaction scheme shown in the following [Formula 4] and [Formula 5], an amine derivative (II) prepared from glycidyl ether and ethanolamine is reacted with a hydroxy fatty acid ester (III), the hydroxyl group of which is protected with an ether-base protecting group $R^7$ such as a tetrahydropyranyl group or an ethoxyethyl group, in the presence of a base catalyst to thereby give an amide derivative (IV). Next, two hydroxyl groups of the amide derivative (IV) are protected with acetyl groups or tert-butyldiphenylsilyl groups (protecting groups $R^8$) and the protecting group $R^7$ is eliminated by treating with an alcohol in the presence of an acid catalyst to thereby give an amide derivative (VI). Then the amide derivative (VI) is treated with a carboxylic acid (VII) in the presence of an appropriate (wherein $R^1$, $R^2$ and $R^3$ are as defined above; $R^6$ represents a lower alkyl group; $R^7$ represents

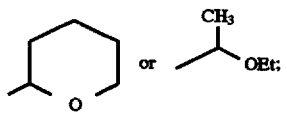

and $R^8$ represents an acetyl group or a tert-butyldiphenylsilyl group).

[Formula 6]

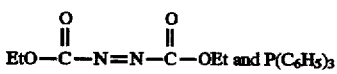

The carboxylic acid (VII) and the acid chloride (VIII) containing the hydrocarbon group represented by $R^3$ to be used here can be prepared from the corresponding unsaturated fatty acid ester (X-A), epoxy fatty acid ester (X-B) and polyhydroxy fatty acid ester (X-C). When the unsaturated fatty acid ester is one represented by the formula (X-A) in the following [Formula 7], for example, the compounds (VII) and (VIII) can be prepared through the functional group conversion as shown in the following [Formula 7]:

[Formula 7]

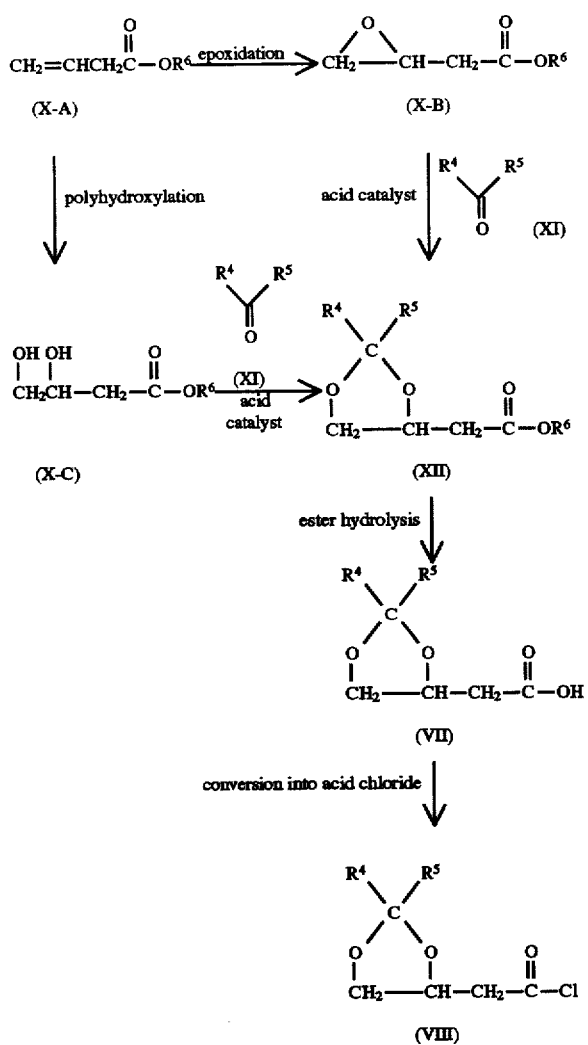

(wherein R⁴, R⁵ and R⁶ are as defined above).

Namely, a carboxylic acid (VII) can be prepared by reacting a marketed epoxy fatty acid ester (X-B) or polyhydroxy fatty acid ester (X-C) or an epoxy fatty acid ester (X-B) or polyhydroxy fatty acid ester (X-C), which are synthesized from an unsaturated fatty acid ester (X-A) with the use of a peracid or a metal oxide catalyst, with a ketone or an aldehyde (XI) in the presence of an acid catalyst and then hydrolyzed by treating with a base in an alcohol. A carboxylic acid chloride (VIII) can be prepared by treating the carboxylic acid (VII) with, for example, thionyl chloride.

(2) Method for preparing an amide derivative (I-B) of the general formula (I) wherein X is —CH₂—:

In accordance with the reaction scheme as shown in the following [Formula 8], a carboxylic ester (XII) or a carboxylic acid (VII) used in the above method (1) is converted into an alcohol (XIII) by using a reducing agent such as lithium aluminum hydride. Then the alcohol (XIII) is converted into a corresponding sulfonate (XIV) by treating with p-toluenesulfonyl chloride. In the presence of a base, the sulfonate (XIV) is reacted with a hydroxy fatty acid ester to thereby synthesize an etherified fatty acid ester (XV), which is then treated with an amide derivative (II) used in the above method (1). Thus the aimed amide derivative (I-B) is obtained.

[Formula 8]

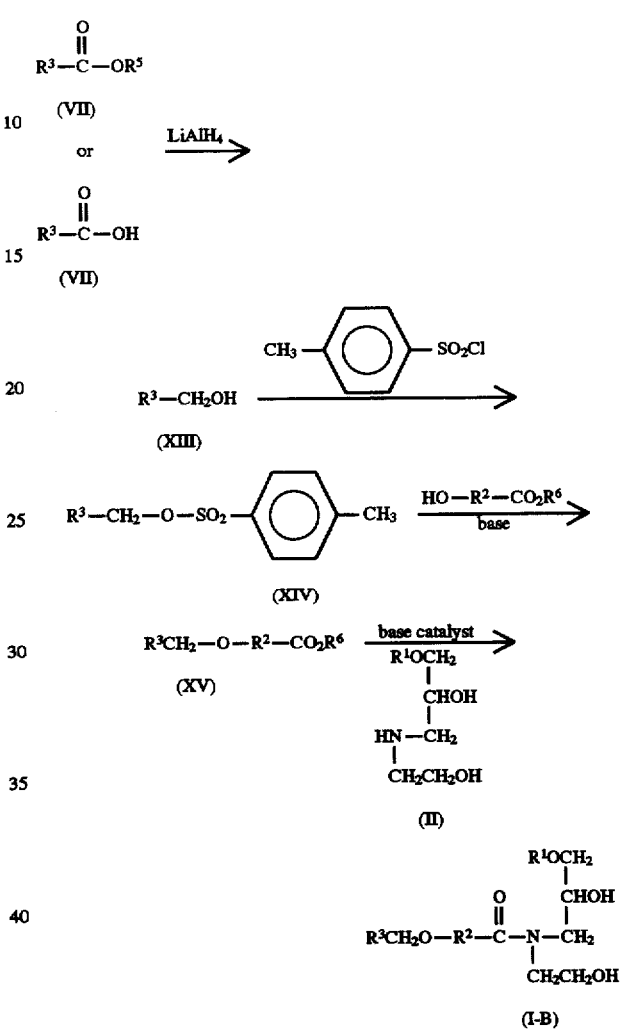

(wherein R¹, R², R³ and R⁶ are as defined above).

Next, the amide derivative according to the present invention represented by the above general formula (II) will be described in detail.

In the amide derivative according to the present invention represented by the above general formula (II), R¹¹ in the general formula (II) represents a straight-chain or branched hydrocarbon group carrying 10 to 40 carbon atoms. Particular examples of said hydrocarbon group include decyl, dodecyl, tetradecyl, hexadecyl, octadecyl, docosyl, dotriacontyl, methyl-branched isostearyl, 2-ethylhexyl, 2-heptylundecyl and 9-octadecenyl groups. As R¹¹, straight-chain hydrocarbon groups carrying 12 to 18 carbon atoms, from among the above-mentioned ones, are preferable and tetradecyl, hexadecyl and octadecyl groups are particularly preferable.

R¹² represents a straight-chain or branched hydrocarbon group carrying 1 to 39 carbon atoms. Particular examples of said hydrocarbon group include methylene, dimethylene, trimethylene, tetramethylene, pentamethylene, octamethylene, decamethylene, undecamethylene, tetradecamethylene, pentadecamethylene, nonacosamethylene, heptadecane-1,11-diyl and 8-heptadecene-1,11-diyl groups. As $R^{12}$, straight-chain hydrocarbon groups carrying 5 to 15 carbon atoms, from among the above-mentioned ones, are preferable and decamethylene and undecamethylene groups are particularly preferable.

$R^{13}$ represents a hydrogen atom or hydrocarbon group carrying 1 to 6 carbon atoms. As $R^{13}$, a hydrogen atom is preferable. Particular examples of the hydrocarbon group represented by $R^{13}$ include methyl, ethyl, propyl, butyl, hexyl and allyl groups.

$R^{14}$ represents a hydrogen atom or a hydrocarbon group having a straight-chain, branched or cyclic structure and carrying 1 to 40 carbon atoms which may contain an oxygen atom. Particular examples of said hydrocarbon group include methyl, propyl, pentyl, heptyl, nonyl, undecyl, tridecyl, pentadecyl, heptadecyl, hentriacontyl, methyl-branched isoheptadecyl, 3-heptyl, 8-heptadecyl, 8-heptadecenyl, 8,11-heptadecadienyl, 8,11,14-heptadecatrienyl, cholesteryl, 8-hydroxyoctyl, 11-hydroxyundecyl, 14-hydroxytetradecyl, 15-hydroxypentadecyl, 11-hydroxyheptadecyl, 11-hydroxy-8-heptadecenyl, 8,9-dihydroxyheptadecyl, 11,12-dihydroxy-8-heptadecenyl, 11-methoxyheptadecyl, 11-ethoxyheptadecyl, 11-methoxy-8-heptadecenyl, 9,10-(isopropylidenedioxy)decyl, 8,9-(isopropylidenedioxy) heptadecyl, 8,9:11,12-bis(isopropylidenedioxy)heptadecyl, 8,9:11,12:14,15-tris(isopropylidenedioxy)heptadecyl, 11,12-(isopropylidenedioxy)-8-heptadecenyl, 8-(6-hydroxyhexyloxy)octyl, 8-[2-(hexyloxy)ethoxy]octyl, 10-[2-(hexyloxy)ethoxy]decyl, 10-[2-(butoxy)ethoxy]decyl, 14-[2-(hexyloxy)ethoxy]tetradecyl, 14-[2-(2-hydroxyethoxy)ethoxy]tetradecyl, 14-[2-(butoxy)ethoxy] tetradecyl, 14-[polyoxypropylene(5)]tetradecyl, 8-[6-(2-hydroxyethoxy)hexyloxy]-octyl, 11-[2-(2-hydroxyethoxy) ethoxycarbonyl]undecyl, 11-[2-(hexyloxy)ethoxycarbonyl] undecyl and 11-acetoxy-8-heptadecenyl groups. As $R^{14}$, groups having a structure represented by the following [Formula 9], from among the above-mentioned ones, are preferable and 8-heptadecenyl, 8,11-heptadecadienyl, 8,11, 14-heptadecatrienyl, 11-hydroxyundecyl, 14-hydroxytetradecyl, 15-hydroxy-pentadecyl, 11-hydroxyheptadecyl, 11-hydroxy-8-heptadecenyl, 8,9-11,12-dihydroxyheptadecyl, 11,12-dihydroxy-8-heptadecenyl, 11-methoxyheptadecyl, 11-ethoxyheptadecyl, 11-methoxy-8-heptadecenyl, 8,9-(isopropylidenedioxy)heptadecyl, 8,9:11,12-bis(isopropylidenedioxy)-heptadecyl, 8,9:11, 12:14,15-tris(isopropylidenedioxy)-heptadecyl, 11,12-(isopropylidenedioxy)-8-heptadecenyl, 8-(6-hydroxyhexyloxy)octyl, 8-[2-(hexyloxy)ethoxy]-octyl, 10-[2-(hexyloxy)ethoxy]decyl, 10-[2-(butoxy)ethoxy]decyl, 14-[2-(hexyloxy)ethoxy]tetradecyl, 14-[2-(2-hydroxyethoxy)ethoxy]tetradecyl, 8-[6-(2-hydroxyethoxy) hexyloxy]octyl, 14-[2-(butoxy)ethoxy]tetradecyl and 14 -[polyoxypropylene(5)]tetradecyl groups may be cited as still preferable examples thereof.

$R^{14}=R^{14'}$—$(CH_2)_n$—[Formula 9]

(wherein n is an integer of from 7 to 15; and $R^{14'}$ represents a hydrocarbon group having at least one double bond, hydroxyl group or ether oxygen atom and carrying 6 to 15 carbon atoms).

Among the amide derivatives of the present invention represented by the above general formula (II), the most preferable compounds are those represented by the general formula (II) wherein each of the $R^{11}$, $R^{12}$, $R^{13}$ and $R^{14}$ groups is one selected from the corresponding ones falling within the most preferable ranges as specified above.

Methods for preparing the amide derivative of the present invention represented by the above general formula (II) are not particularly restricted. For example, it can be synthesized by a method in accordance with a reaction scheme shown in the following Formula 10.

[Formula 10]

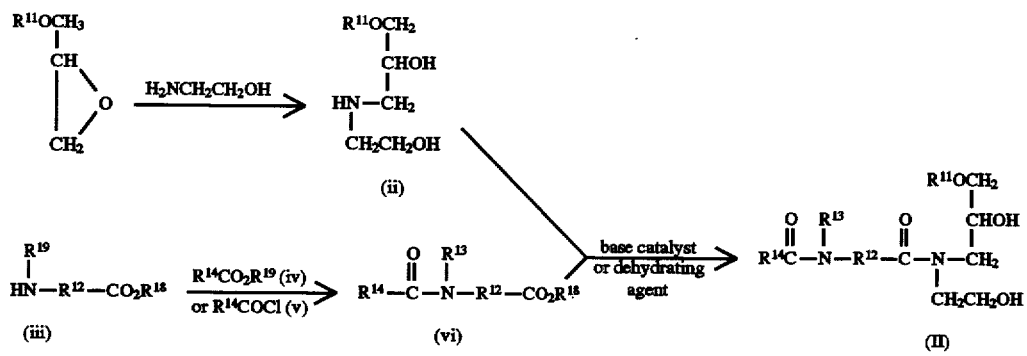

(wherein $R^{18}$ and $R^{19}$ represents each a hydrogen atom or a lower alkyl group; and other symbols are as defined above).

According to the reaction scheme shown in the above Formula 10, an amine (ii), which has been prepared from glycidyl ether and ethanolamine, is reacted with an amido carboxylic acid or its ester (vi), which has been prepared by condensing a carboxylic acid or its ester (iv) or an acid chloride (v) with an amino carboxylic acid or its ester (iii) without using any catalyst or in the presence of a catalyst such as an acid or a base or in the presence of a dehydrating agent such as dicyclohexylcarbodiimide, in the presence of a base catalyst or a dehydrating agent such as dicyclohexylcarbodiimide. Thus the amide derivative (II) of the present invention can be obtained.

Next, the dermatologic preparation of the present invention containing the amide derivative of the present invention represented by the above general formula (I) or (II) will be described.

The dermatologic preparations according to the present invention are obtained by blending a base commonly used for dermatologic preparations with the amide derivatives of the present invention represented by the above-mentioned general formula (I) or (II). These dermatologic preparations may be broadly classified into medicinal dermatologic preparations and cosmetics depending on the applications thereof.

Examples of the medicinal dermatologic preparations include various ointments containing medicinal ingredients. These ointments may contain either an oily base or an O/W or W/O emulsion base. The oily base is not particularly restricted and examples thereof include vegetable oils, animal oils, synthetic oils, fatty acids, and natural and synthetic glycerides. The medicinal ingredients are not particularly restricted and, for example, analgesics, antiinflammatory agents, antipruritic agents, bactericides, astringents, skin emollients and hormones may be used therefor, if required.

In using the dermatologic preparations of the present invention as the cosmetic, the essential ingredient, i.e., the amide derivative of the present invention may be arbitrarily blended with, for example, oleaginous components, humectants, ultraviolet absorbers, whitening agents, alcohols, chelating agents, pH modifiers, preservatives, thickeners, colorants and perfumes commonly employed in the art.

The dermatologic preparations may be formulated into various skin cosmetics including W/O and O/W emulsion cosmetics, cream, cosmetic milky lotion, cosmetic lotion, oily cosmetic, lipstick, foundation, skin cleanser, hair tonic, hair styling lotion, hair nourishment and hair growth stimulant.

The content of the amide derivative of the present invention in the dermatologic preparation of the present invention is not particularly restricted. In the case of an emulsion type preparation, the amide derivative may be preferably contained in an amount of 0.001 to 50% (by weight, the same will apply hereinafter) based on the whole preparation. In the case of an oily preparation containing a liquid hydrocarbon, such as squalane, as a base, the amide derivative may be preferably contained in an amount of 0.01 to 50%.

The function mechanism of the dermatologic preparations of the present invention containing the amide derivatives of the present invention represented by the above general formula (I) or (II) has not been completely clarified in detail. It is assumed, however, that when applied to the skin as the dermatologic preparation, the amide derivative of the present invention would penetrate into liquid membranes between the horny layers so as to improve (maintain and reinforce) the barrier functions of the horny layer.

To further illustrate the present invention in greater detail, the following Examples will be given.

EXAMPLE 1

Synthesis of Amide Derivative (I-Aa) [Amide Derivative Represented by the Above General Formula (I) Wherein $R^1$, $R^2$ and $R^3$-X are Those Represented by the Following [Formula 11]]:

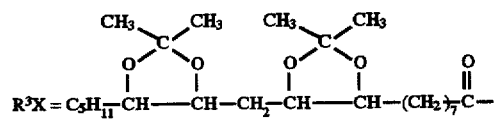

[Formula 11]

(1) Synthesis of 1-(2-hydroxyethylamino)-3-hexadecyloxy-2-propanol (II-a):

916.2 g (15 mol) of ethanolamine and 183 g of ethanol were introduced into a 3-1 five-necked flask equipped with a stirrer, a dropping funnel, a thermometer, a nitrogen inlet and a distilling tube and heated to 80° C. under a nitrogen atmosphere, while dropping 298.6 g (1 mol) of hexadecyl glycidyl ether thereto over a period of 3 hours. After the completion of the addition, the ethanol and the excessive ethanolamine were distilled off under reduced pressure and the residue was recrystallized from methanol. Thus 331.0 g of the title compound (II-a) was obtained as a colorless powder (yield: 92.0%).

(2) Synthesis of N-(2-hydroxy-3-hexadecyloxypropyl)-N-2-hydroxyethyl-16-(2-tetrahydropyranyloxy)-hexadecanamide (IV-a):

100.26 g (0.35 mol) of methyl 16-hydroxyhexadecanoate, 0.60 g (3.5 mmol) of p-toluenesulfonic acid and 350 ml of dichloromethane were introduced into a 1-1 flask equipped with a stirrer and a dropping funnel and 32.39 g (0.385 mol) of dihydropyan was dropped thereto under stirring at 0° C. After the completion of the addition, the mixture was stirred at room temperature for additional 1 hour to thereby complete the reaction. Next, the reaction mixture was neutralized by adding 0.59 g (7 mmol) of $NaHCO_3$ and filtered. After distilling off the solvent, crude methyl 16-(2-tetrahydropyranyloxy)hexadecanoate (III-a) was obtained.

Subsequently, 125.9 g (0.35 mol) of the compound (II-a) obtained in the above (1) and 0.98 g (17.5 mmol) of KOH were introduced into a 1-1 flask equipped with a stirrer, a dropping funnel, a thermometer and a distilling tube. Then the crude methyl 16-(2-tetrahydropyranyloxy) hexadecanoate (III-a) obtained above was dropped thereto over a period of 2 hours while heating and stirring under a reduced pressure (80° C./20 Torr). During this reaction period, the methanol thus formed was distilled off. After the completion of the addition, stirring was continued under the same conditions for additional 2 hours. The crude product thus obtained was recrystallized from methanol. Thus 212.3 g of the title compound (IV-a) was obtained (yield: 86.9%).

(3) Synthesis of N-(2-acetoxy-3-hexadecyloxypropyl)-N-2-acetoxyethyl-16-hydroxyhexadecanamide (VI-a):

160.6 g (0.23 mol) of the compound (IV-a) obtained in the above (2), 91.0 g (1.15 mol) of pyridine and 440 ml of dichloromethane were introduced into a 1-1 flask provided with a stirrer and a dropping funnel. Then 45.1 g (0.575 mol) of acetyl chloride was dropped thereto over a period of 1.5 hours under stirring at 0° C. After the completion of the addition, the reaction was continued for additional 1 hour to thereby complete the same. Next, 7.4 g (0.23 mol) of methanol was added to the reaction mixture and reacted with the excessive acetyl chloride. The resulting mixture was washed with water, 2N-hydrochloric acid and an aqueous solution of common salt and the solvent was distilled off. Thus an intermediate (V-a) was obtained.

Subsequently, the intermediate (V-a) obtained above was introduced into a 1-1 flask equipped with a stirrer and 368 g (0.115 mol) of methanol and 1.16 g (4.6 mmol) of pyridinium p-toluenesulfonate were added thereto and stirred at 40° C. for 5 hours. After the completion of the reaction, the reaction mixture was neutralized by adding 0.76 g (9.2 mmol) of $NaHCO_3$. The methanol was distilled off and the residue was dissolved in chloroform and washed with an aqueous solution of common salt. After distilling off the solvent, the residue was purified by silica gel short column chromatography. Thus 131.0 g of the title compound (VI-a) was obtained (yield: 81.6%).

(4) Synthesis of 9,10:12,13-bis(isopropylidenedioxy)octadecanoic acid (VII-a):

147.2 g (0.5 mol) of methyl linoleate, 203.2 g (1.18 mol) of m-chloroperbenzoic acid and 500 ml of dichloromethane were introduced into a 2-1 flask equipped with a stirrer and stirred at room temperature for 18 hours. After the completion of the reaction, the m-chlorobenzoic acid thus precipitated was separated by filtration and the residue was washed with an aqueous solution of sodium thiosulfate. After distilling off the solvent under reduced pressure, the residue was purified by alumina short column chromatography. Thus an intermediate (X-B) was obtained.

Subsequently, 1162 g (20 mol) of acetone and 3.55 g (25 mmol) of a boron trifluoride-ether complex were introduced into a 2-l flask equipped with a stirrer and a dropping funnel. Then the intermediate (X-B) obtained above was dropped thereto over a period of 3 hours while stirring at room temperature. After the completion of the addition, the mixture was stirred for additional 1 hour to thereby complete the reaction. Next, the reaction mixture was neutralized by adding $NaHCO_3$ and the solvent was distilled off under reduced pressure. The residue was purified by silica gel chromatography and thus 201.2 g of methyl 9,10:12,13-bis(isopropyl-idenedioxy)octadecanoate (XII-a) was obtained (yield: 90.9%).

Subsequently, 141.6 g (0.32 mol) of the compound (XII-a) thus obtained and 400 ml of ethanol were introduced into a 2-l flask equipped with a stirrer. Then a solution of 35.8 g (0.64 mol) of KOH in 40 ml of water and 400 ml of ethanol was added thereto and stirred at 50° C. for 1 hour. Next, this reaction mixture was neutralized with hydrochloric acid and extracted with chloroform. After distilling off the solvent under reduced pressure, the residue was purified by silica gel chromatography. Thus 132.0 g of the title compound (VII-a) was obtained (yield: 96.3%).

(5) Synthesis of amide derivative (I-Aa):

22.34 g (32 mmol) of the compound (VI-a) obtained in the above (3), 16.46 g (38.4 mmol) of the compound (VII-a) obtained in the above (4), 11.75 g (44.8 mmol) of triphenylphosphine and 100 ml of tetrahydrofuran were introduced into a 300-ml flask equipped with stirrer and a dropping funnel. Then 6.69 g (38.4 mmol) of diethyl azodicarboxylate was dropped thereto over a period of 30 minutes under stirring at 15° C. After the completion of the addition, the mixture was stirred for additional 3 hours at room temperature. Then the solvent was distilled off from the reaction mixture under reduced pressure and the residue was purified by silica gel chromatography. Thus an intermediate (IX-a) was obtained.

Subsequently, the intermediate (IX-a) thus obtained was introduced into a flask equipped with a stirrer and 200 ml of methanol, 400 ml of ethanol and 7.39 g (53.5 mmol) of $K_2CO_3$ were added thereto. After stirring at 15° C. for 30 minutes, water was added to the reaction mixture to thereby dissolve the salt thus formed. After extracting with diisopropyl ether and distilling off the solvent under reduced pressure, the residue was purified by silica gel chromatography. Thus 23.25 g of the target amide derivative (I-Aa) was obtained (yield: 69.3%).

The melting point and IR and $^1$H-NMR data of the obtained amide derivative are as follows:

m.p.: 50.4°–52.1° C. IR: 3308, 2920, 2856, 1730, 1608, 1464, 1438, 1370, 1220, 1172, 1096, 1058 cm$^{-1}$ $^1$H-NMR: (δ, $CDCl_3$); 0.82–0.96 (m,6H), 1.13–1.84 (m, 88H), 2.28 (t, J=7.5Hz, 2H), 2.39 (t, J=7.5 Hz, 2H), 3.20–4.20 (m, 17H), 4.05 (t, J=6.6Hz, 2H)

EXAMPLE 2

Synthesis of Amide Derivative (I-Ab) [Amide Derivative Represented by the Above General Formula (I) Wherein $R^1$, $R^2$ and $R^3$-X are Those Represented by the Following [Formula 12]]:

$R^1 = C_{16}H_{33}-$,  [Formula 12]

$R^2 = -(CH_2)_{14}-$,

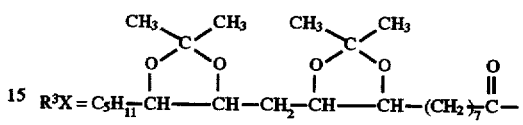

The procedure of Example 1 was repeated except that the methyl 16-hydroxyhexadecanoate employed in Example 1 was replaced by methyl 15-hydroxypentadecanoate. Thus the target amide derivative (I-Ab) was obtained.

The melting point and IR and $^1$H-NMR data of the obtained amide derivative are as follows:

m.p.: 55.8°–58.0° C.

IR: 3312, 2948, 2904, 2856, 1728, 1610, 1464, 1370, 1218, 1168, 1108, 1054 cm$^{-1}$ $^1$H-NMR: (δ, $CDCl_3$); 0.80–1.11 (m,6H), 1.11–1.90 (m, 86H), 2.28 (t, J=7.5Hz, 2H), 2.39 (t, J=7.7 Hz, 2H), 3.21–4.20(m, 17H), 4.05 (t, J=6.7Hz, 2H)

EXAMPLE 3

Synthesis of Amide Derivative (I-Ac) [Amide Derivative Represented by the Above General Formula (I) Wherein $R^1$, $R^2$ and $R^3$-X are Those Represented by the Following [Formula 13]]:

$R^1 = C_{16}H_{33}-$,  [Formula 13]

$R^2 = -(CH_2)_{15}-$,

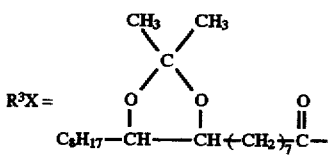

The procedure of Example 1 was repeated except that the methyl linoleate employed in Example 1 was replaced by methyl oleate. Thus the target amide derivative (I-Ac) was obtained.

The melting point and IR and $^1$H-NMR data of the obtained amide derivative are as follows:

m.p.: 57.8°–59.2° C.

IR: 3348, 2920, 2856, 1732, 1612, 1464, 1436, 1368, 1240, 1178, 1104, 1060 cm$^{-1}$ $^1$H-NMR: (δ, $CDCl_3$); 0.78–1.00 (m,6H), 1.08–1.69 (m, 86H), 2.25 (t, J=7.5Hz, 2H), 2.35 (t, J=7.6 Hz, 2H), 3.16–4.18 (m, 15H), 4.01 (t, J=6.7Hz, 2H)

EXAMPLE 4

Syntheses of Amide Derivative (I-Ba) [Amide Derivative Represented by the Above General Formula (I) Wherein $R^1$, $R^2$ and $R^3$-X are Those Represented by the Following [Formula 14]]:

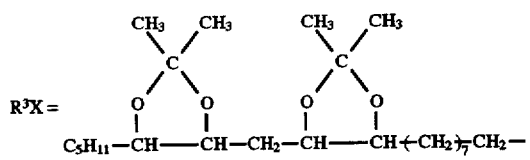

2.28 g (60 mmol) of LiAlH$_4$ and 200 ml of tetrahydrofuran were introduced into a 500-ml flask equipped with a stirrer and a dropping funnel. Under stirring, a solution of 21.43 g (50 mmol) of 9,10:12,13-bis(isopropylidenedioxy)octadecanoic acid (VII-a) obtained in the above Example 1 (4) in 50 ml of tetrahydrofuran was dropped thereto over a period of 20 minutes. After the completion of the addition, stirring was continued at 60° C. for additional 3 hours to thereby complete the reaction. The reaction mixture was cooled and the excessive LiAlH$_4$ was decomposed by adding 7 ml of a 5% aqueous solution of KOH. After separating the salt thus precipitated, the solvent was distilled off under reduced pressure.

Subsequently, the above-mentioned residue was transferred into a 200-ml flask equipped with a stirrer and 40 ml of pyridine and 14.3 g (75 mmol) of p-toluenesulfonyl chloride were added thereto at 0° C., followed by stirring at 0° C. for 3 hours. After adding chloroform to the reaction mixture, the resulting mixture was washed with an aqueous solution of common salt and the solvent was distilled off under reduced pressure. Thus an intermediate (XIV-a) was obtained.

Subsequently, the intermediate (XIV-a) thus obtained, 47.2 g (150 mmol) of isopropyl 16-hydroxyhexadecanoate, 250 ml of tetrahydrofuran, 50 ml of hexamethylphosphoryltriamide and 10 g (250 mmol) of sodium hydride were introduced into a 1-l flask equipped with a stirrer and stirred at 60° C. for 3 hours. Then 250 ml of methanol was added to the reaction mixture, followed by stirring at 60° C. for 1 hour. The reaction mixture was cooled to room temperature, neutralized by adding an aqueous solution of NH$_4$Cl and extracted with diisopropyl ether. After distilling off the solvent under reduced pressure, the residue was purified by silica gel chromatography. Thus an intermediate (XV-a) was obtained.

Subsequently, 16.5 g (45.9 mmol) of the compound (II-a) obtained in the above Example 1 (1) and the intermediate (XV-a) obtained above were introduced into a 200-ml flask equipped with a stirrer, a dropping funnel and a distilling tube and a 28% solution of sodium methoxide in methanol was added thereto under heating to 80° C. and stirring. Then the resulting reaction mixture was evacuated to 20 Torr at 80° C. and heated and stirred for 3 hours while distilling off the methanol thus formed. After the completion of the reaction, the reaction mixture was purified by silica gel chromatography. Thus 20.6 g of the target amide derivative (I-Ba) was obtained (yield: 40.8%).

The melting point and IR and $^1$H-NMR data of the obtained amide derivative are as follows:

m.p.: 55.2°–56.7° C.

IR: 3312, 2920, 2852, 1618, 1464, 1372, 1296, 1104, 1050 cm$^{-1}$ $^1$H-NMR: (δ, CDCl$_3$); 0.78–1.00 (m,6H), 1.08–1.85 (m, 90H), 2.39 (t, J=7.4Hz, 2H), 3.17–4.20 (m, 17H), 3.38 (t, J=6.8Hz, 4H)

EXAMPLE 5

The dermatologic preparations of the present invention comprising 10% of each of the amide derivatives of the present invention listed in Table 1 and 90% of squalane were prepared. Then the transepidermal water loss and percutaneous absorption of each dermatologic preparation were evaluated in the following manner. For comparison, a comparative dermatologic preparation comprising squalane alone was also evaluated. Table 1 summarizes the results.

(Test method)

Wistar male rats were fed with a feed free from essential fatty acids and the rats with essential fatty acid deficiency were employed in this test. The dorsal part of the rat showing essential fatty acid deficiency was carefully shaven and each dermatologic preparation was applied thereto once a day for 3 weeks. A group having 5 animals was used for each dermatologic preparation. After 3 weeks, the following items were examined.

(1) Transepidermal water loss

The dorsal skin of the test rat was washed with warm water and the animal was then allowed to stand in a room at 23° C. under a humidity of 45% for 1 hour. Then the transepidermal water loss was measured with an evaporimeter. When the normal barrier functions are maintained, the transepidermal water loss is usually smaller than 10. On the other hand, a rat with essential fatty acid deficiency shows a higher value of 20 to 30. This is seemingly because the amount of the water transepidermally evaporated is increased due to the damaged barrier functions of the horny layer. Thus a larger water loss means lower barrier functions of the horny layer and more serious chapping. Accordingly, the effects of the invention products as a dermatologic preparation can be discussed by measuring the transepidermal water loss.

Each value is expressed in "mean±standard deviation".

(2) Percutaneous adsorption

The dorsal skin of the rat was washed with water at 37° C. Next, said skin was cut and inserted into a percutaneous absorption chamber with the epidermal side thereof directed upward. A lower receiver of the chamber was filled with a phosphate buffer equilibrated salt solution while a container on the epidermal side thereof was charged with 1 ml of a phosphate buffer equilibrated salt solution containing 37KBq of $^{14}$C-salicylic acid. After 2 hours, the amount of the $^{14}$C-salicylic acid penetrating into the lower receiver was determined. When the normal barrier functions are maintained, the $^{14}$C-salicylic acid scarcely penetrates after 2 hours (i.e., the test period employed herein). In the case of an essential fatty acid deficient rat with damaged barrier functions, however, the amount of the penetrating $^{14}$C-salicylic acid is significantly increased. Each value is expressed in "mean±standard deviation".

TABLE 1

| | Amide derivative | Transepidermal water loss | Percutaneous absorption |
| --- | --- | --- | --- |
| Product of Invention | compound of Ex. 1 | 12.3 ± 4.1 | 348 ± 127 |
| | compound of Ex. 2 | 17.2 ± 6.4 | 513 ± 260 |

TABLE 1-continued

| | Amide derivative | Transepidermal water loss | Percutaneous absorption |
|---|---|---|---|
| | compound of Ex. 3 | 18.9 ± 4.9 | 793 ± 211 |
| | compound of Ex. 4 | 11.0 ± 3.2 | 367 ± 164 |
| Comparison | squalane alone | 34.4 ± 5.8 | 1487 ± 289 |

As the results given in the above Table 1 clearly show, each of the invention products containing the amide derivative of the present invention significantly suppressed both of the transepidermal water loss and percutaneous absorption, compared with the comparative product comprising squalane alone.

EXAMPLE 6

By using each of the amide derivatives of the present invention, the dermatologic preparations (emulsion cosmetic) of the present invention of the compositions as specified in the following Table 2 were prepared. The effect of each product of improving skin chapping was evaluated in the following manner. For comparison, a dermatologic preparation free from any amide derivative of the present invention (comparative product) was evaluated in the same manner. Table 3 summarizes the results.

(Test method)

Twenty healthy female subjects aged 20 to 50 years, who suffered from chapping in cheeks in winter, were employed. Different dermatologic preparations were applied on the right and left cheeks of the subjects once a day for 3 weeks. After 3 weeks, the following items were examined.

(1) Transepidermal water loss

The face of each subject was washed with water at 37° C. and then she was allowed to stand in a room at 20° C. under a humidity of 45% for 1 hour. Then the transepidermal water loss from the cheeks was measured with an evaporimeter. A larger water loss means lower barrier functions of the horny layer and more serious chapping. When scarcely any chapping is observed, this value is smaller than 10. In the case of serious chapping, on the other hand, this value is 2 to 4 times as high as the normal level. Each value was expressed in "means±standard deviation".

(2) Skin chapping score

Skin chapping was observed with the naked eye and evaluated based on the following criteria. Each score is expressed in "mean±standard deviation".

| score | evaluation of chapping |
|---|---|
| 0 | no chapping observed. |
| 1 | slight chapping observed. |
| 2 | chapping observed. |
| 3 | somewhat serious chapping observed. |
| 4 | serious chapping observed. |

TABLE 2

| | Invention product | (% by weight) Comparative product |
|---|---|---|
| methyl-branched isostearyl glyceryl ether | 2.0 | 2.0 |
| 2-octyldodecyl myristate | 10.0 | 10.0 |
| vaseline | 3.0 | 3.0 |
| squalane | 5.0 | 5.0 |
| tocopherol acetate | 0.5 | 0.5 |
| amide, derivative (refer to Table 2) | 1.0 | — |
| water | the balance | the balance |

TABLE 3

| | Amide derivative | Transepidermal water loss | Skin chapping score |
|---|---|---|---|
| Product of Invention | compound of Ex. 1 | 14.0 ± 2.7 | 0.9 ± 0.4 |
| | compound of Ex. 2 | 16.3 ± 4.0 | 1.1 ± 0.4 |
| | compound of Ex. 3 | 15.9 ± 4.9 | 1.3 ± 0.6 |
| | compound of Ex. 4 | 13.3 ± 3.9 | 0.7 ± 0.3 |
| Comparison | squalane alone | 27.9 ± 7.2 | 2.9 ± 0.6 |

EXAMPLE 7

Synthesis of Amide Derivative (II-a) [Amide Derivative Represented by the Above General Formula (II) Wherein $R^{11}$, $R^{12}$, $R^{13}$ and $R^{14}$ are Those Represented by the Following Formula 15]:

$R^{11} = C_{16}H_{33}-$ [Formula 15]

$R^{12} = -(CH_2)_{10}-$ $R^{13} = H$

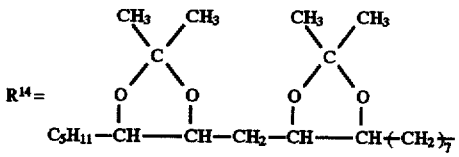

(1) Synthesis of 1-(2-hydroxyethylamino)-3-hexadecyloxy-2-propanol (ii-a):

331.0 g of the title compound (ii-a) was obtained as a colorless powder (yield: 92.0%) according to the method for preparation of Example 1 (1).

(2) Synthesis of 9,10:12,13-bis(isopropylidenedioxy)octadecanoic acid (iv-a):

132.0 g of the title compound (iv-a) was obtained (yield: 96.3%) according to the method for preparation of Example 1 (4).

(3) Synthesis of methyl 11-aminoundecanoate (iii-a):

201.3 g (1 mol) of 11-aminoundecanoic acid, 1600 g of methanol and 294 g (3 mol) of phosphoric acid were introduced into a 3-l flask provided with a stirrer and stirred at 60° C. for 18 hours. After allowing to cool, the reaction mixture was neutralized with an aqueous solution of NaOH and an aqueous solution of $NaHCO_3$ and extracted with chloroform. Then the solvent was distilled off under reduced pressure and the residue was purified by alumina short column chromatography. Thus 200.2 g of the title compound (iii-a) was obtained (yield: 93.0%).

(4) Syntheses of methyl 11-[9,10:12,13-bis(isopropylidenedioxy)octadecanoylamino]undecanoate (vi-a):

34.3 g (80 mmol) of the compound (iv-a) obtained in the above (2), 21.5 g (100 mmol) of the compound (iii-a) obtained in the above (3), 18.4 g (120 mmol) of 1-hydroxybenzotriazole and 500 ml of chloroform were introduced into a 1-l flask provided with a stirrer. Under stirring at room temperature, 33.0 g of N,N'-dicyclohexylcarbodiimide was added thereto and the resulting mixture was stirred at room temperature for additional 24 hours. After the completion of the reaction, the white solid thus precipitated was separated by filtering. After concentrating under reduced pressure, the residue was purified by silica gel chromatography. Thus 31.1 g of the title compound (vi-a) was obtained (yield: 62.1%).

(5) Synthesis of amide derivative (II-a):

9.0 (25.1 mmol) of the compound (ii-a) obtained in the above (1) and 10.5 g (16.7 mmol) of the compound (vi-a) obtained in the above (4) were introduced into a 100-ml flask provided with a stirrer, a dropping funnel and a distilling tube and 0.32 g (1.67 mmol) of a 28% solution of sodium methoxide in methanol was dropped thereto under stirring under a nitrogen atmosphere at 80° C. After the completion of the addition, the mixture was stirred at 80° C. for 1 hour and then under reduced pressure (10 Torr) at 80° C. for additional 1 hour to thereby complete the reaction. After cooling, the reaction mixture was purified by silica gel column chromatography. Thus 13.3 g of the target amide derivative (II-a) was obtained (yield: 83.5%).

The physical properties of the amide derivative (II-a) thus obtained are as follows:

A page yellow solid.
m.p.: 59.7°–61.0° C.
IR (neat, cm$^{-1}$): 3312, 2924, 2856, 1638, 1614, 1546, 1464, 1374, 1214, 1168, 1106, 1060
$^1$H-NMR: (CDCl$_3$, δ): 0.82–1.02 (m,6H), 1.13–1.97 (m, 78H), 2.15 (t, J=7.5Hz, 2H), 2.40 (t, J=7.6 Hz, 2H), 3.18–4.23 (m, 19H), 5.49 (br, 1H)

EXAMPLE 8

Synthesis of Amide Derivative (II-c) [Amide Derivative Represented by the Above General Formula (II) Wherein $R^{11}$, $R^{12}$, $R^{13}$ and $R^{14}$ are Those Represented by the Following Formula 16]:

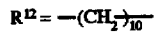
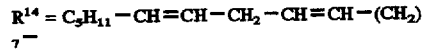

[Formula 16]

(1) Synthesis of methyl 11-linoleoylaminoundecanoate (vi-c):

5.73 g (25 mmol) of the compound (iii-a) obtained in the above Example 7 (3), 3.95 g (50 mmol) of pyridine and 100 ml of dichloromethene were introduced into a 200-ml flask provided with a stirrer and a dropping funnel and 8.22 g (27.5 mmol) of a linoleoyl chloride was dropped thereto under stirring at room temperature over 1 hour. After the completion of the addition, the mixture was stirred at room temperature for additional 24 hours to thereby complete the reaction. After washing with a saturated aqueous solution of common salt, the reaction mixture was concentrated under reduced pressure and the residue was purified by silica gel column chromatography. Thus 9.52 g of the target compound (vi-c) was obtained (yield: 77.4%).

(2) Synthesis of amide derivative (II-c):

The procedure of Example 7 was repeated except that the compound (vi-a) employed in Example 7 (5) was replaced by the compound (vi-c) obtained above. Thus the target amide derivative (II-c) was obtained.

The physical properties of the amide derivative (II-c) thus obtained are as follows:

A colorless solid.
m.p.: 81.4°–82.5° C.
IR (neat, cm$^{-1}$): 3316, 2924, 2852, 1640, 1612, 1546, 1466, 1434, 1110, 1058
$^1$H-NMR (CDCl$_3$, δ): 0.80–1.06 (m,6H), 1.08–1.80 (m, 60H), 1.92–2.12 (m, 4H), 2.15 (t, J=7.6Hz, 2H), 2.40 (t, J=7.5Hz, 2H), 2.69–2.84 (m, 2H), 3.14–4.19 (m, 15H), 5.24–5.48 (m, 4H), 5.58 (br, 1H)

EXAMPLE 9

Synthesis of Amide Derivative (II-e) [Amide Derivative Represented by the Above General Formula (II) Wherein $R^{11}$, $R^{12}$, $R^{13}$ and $R^{14}$ are Represented by the Following Formula 17]:

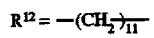

[Formula 17]

The procedure of Example 8 was repeated except that the compound (iii-a) and the linoleoyl chloride (v-c) employed in Example 8 were replaced respectively by methyl 12-aminododecanoate (iii-b) and oleoyl chloride (v-e). Thus the target amide derivative (II-e) was obtained.

The physical properties of the amide derivative (II-e) thus obtained are as follows:

A colorless solid.
m.p.: 82.4°–83.9° C.
IR (neat, cm$^{-1}$): 3312, 2920, 2852, 1608, 1540, 1462, 1108, 1056
$^1$H-NMR (CDCl$_3$, δ): 0.80–1.02 (m, 6H), 1.12–1.87 (m, 68H), 1.90–2.11 (m, 4H), 2.15 (t, J=7.5Hz, 2H), 2.40 (t, J=7.6Hz, 2H), 3.16–4.22 (m, 15H), 5.24–5.57 (m, 3H)

EXAMPLE 10

Synthesis of Amide Derivative (II-f) [Amide Derivative Represented by the Above General Formula (II) Wherein $R^{11}$, $R^{12}$, $R^{13}$ and $R^{14}$ are Represented by the Following Formula 18]:

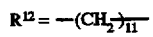
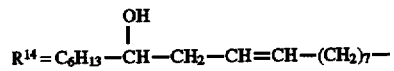

[Formula 18]

The procedure of Example 7 was repeated except that the compound (iv-a) and the compound (iii-a) employed in Example 7 (4) to (5) were replaced respectively by recinolic acid and methyl 12-aminododecagoate (iii-b). Thus the target amide derivative (II-f) was obtained.

The physical properties of the amide derivative (II-f) thus obtained are as follows:

A pale yellow solid.

m.p.: 75.9°–77.9° C.

IR (neat, cm$^{-1}$): 3312, 2912, 2852, 1610, 1542, 1468, 1440, 1374, 1294, 1260, 1220, 1194, 1164, 1108, 1058

$^1$H-NMR (CDCl$_3$, δ): 0.91–1.00 (m,6H), 1.12–1.78 (m, 64H), 1.78–2.48 (m, 9H), 3.16–4.22 (m, 15H), 5.32–5.69 (m, 3H)

EXAMPLE 11

Synthesis of Amide Derivative (II-g) [Amide Derivative Represented by the Above General Formula (II) Wherein $R^{11}$, $R^{12}$, $R^{13}$ and $R^{14}$ are Represented by the Following Formula 19]:

$R^{11} = C_{16}H_{33}-$  [Formula 19]

$R^{12} = -(CH_2)_{11}-$ $R^{13} = H$ $R^{14} = C_6H_{13}-\overset{OCH_3}{\underset{|}{CH}}-CH_2-CH=CH-(CH_2)_7-$ (1) Synthesis of 12-methoxy-9-octadecenoic acid:

24 g (0.6 mol) of sodium hydride and 500 ml of dimethylformamide were introduced into a 1-l flask provided with a stirrer, a dropping funnel and a cooling tube and a solution of 163.3 g (0.5 mol) of ethyl ricinolate in 142 g (1.0 mol) of methyl iodide was dropped thereto under stirring at 40° C. under a nitrogen atmosphere over 1 hour. After the completion of the addition, the mixture was stirred at 40° C. for additional 6 hours. To the obtained reaction mixture was added hexane. After washing with an aqueous solution of ammonium chloride and an aqueous solution of sodium thiosulfate, the mixture was concentrated under reduced pressure and the residue was purified by silica gel column chromatography. Thus 155.8 g of ethyl 12-methoxy-9-octadecenoate was obtained (yield: 91.5%).

Subsequently, 68.1 g (0.2 mol) of the ethyl 12-methoxy-9-octadecenoate obtained above, 600 ml of ethanol and 45 g of a 50% aqueous solution of potassium hydroxide were introduced into a 1-l flask provided with a stirrer and stirred at 50° C. for 4 hours. To the obtained reaction mixture was added hexane. Then the mixture was neutralized with 3N hydrochloric acid and washed with a saturated aqueous solution of common salt. Then it was concentrated under reduced pressure and the residue was purified by silica gel column chromatography. Thus 58.3 g of the title compound (iv-g) was obtained (yield: 93.3%).

(2) Synthesis of amide derivative (II-g):

The procedure of Example 7 was repeated except that the compound (iv-a) and the compound (iii-a) employed in Example 7 (4) to (5) were replaced respectively by the compound (iv-g) obtained above and methyl 12-aminododecanoate (iii-b). Thus the target amide derivative (II-g) was obtained.

The physical properties of the amide derivative (II-g) thus obtained are as follows:

A pale yellow solid.

m.p.: 82.4°–83.9° C.

IR (neat, cm$^{-1}$): 3304, 2896, 2868, 1606, 1542, 1460, 1438, 1102, 1056

$^1$H-NMR (CDCl$_3$, δ): 0.82–0.97 (m, 6H), 1.10–1.73 (m, 70H), 1.88–2.47 (m, 6H), 2.15 (t, J=7.5Hz, 2H), 3.12–4.18 (m, 19H), 5.19–5.71 (m, 3H)

EXAMPLE 12

Synthesis of Amide Derivative (II-h) [Amide Derivative Represented by the Above General Formula (II) Wherein $R^{11}$, $R^{12}$, $R^{13}$ and $R^{14}$ are Represented by the Following Formula 20]:

$R^{11} = C_{16}H_{33}-$  [Formula 20]

$R^{12} = -(CH_2)_{11}-$ $R^{13} = H$ $R^{14} = C_6H_{13}-O-(CH_2)_2CH_2)_{10}-$ (1) Synthesis of methyl 11-(2-hexyloxyethoxy)undecanaote (iv-h):

70.2 g (0.48 mol) of 2-hexyloxyethanol and 60 ml of dimethylformamide were introduced into a 1-l flask provided with a stirrer, a dropping funnel and a cooling tube and 12 g (0.30 mol) of sodium hydride was added thereto under stirring under a nitrogen atmosphere. To the resulting mixture was dropped a solution of 31.8 g (0.12 mol) of 11-bromoundecanoic acid in 90 ml of tetrahydrofuran under stirring and heating to 80° C. After the completion of the addition, the mixture was stirred at 80° C. for additional 4 hours. After the completion of the reaction, the mixture was cooled to room temperature, neutralized with 3N hydrochloric acid and then extracted with isopropyl ether. After distilling off the solvent under reduced pressure, the residue was distilled under reduced pressure (160°–170° C/0.01 Torr). Thus 33.0 g of the title compound (iv-h) was obtained (yield: 83.3%).

(2) Synthesis of amide derivative (II-h):

The procedure of Example 7 was repeated except that the compound (iv-a) and the compound (iii-a) employed in Example 7 (4) to (5) were replaced respectively by the compound (iv-h) obtained in the above (1) and methyl 12-aminododecanoate (iii-b). Thus the target amide derivative (II-h) was obtained.

The physical properties of the amide derivative (II-h) thus obtained are as follows:

A colorless solid.

m.p.: 82.8°–84.2° C.

IR (neat, cm$^{-1}$): 3304, 2920, 2856, 1606, 1536, 1462, 1374, 1214, 1102, 1054

$^1$H-NMR (CDCl$_3$, δ): 0.82–1.01 (m, 6H), 1.12–1.74 (m, 70H), 2.15 (t, J=7.6Hz, 2H), 2.40 (t, J=7.6Hz, 2H), 3.16–4.20 (m, 19H), 3.58 (s, 4H), 5,43–5.58 (m, 1H)

EXAMPLE 13

Synthesis of Amide Derivative (II-j) [Amide Derivative Represented by the Above General Formula (II) Wherein $R^{11}$, $R^{12}$, $R^{13}$ and $R^{14}$ are Represented by the Following Formula 21]:

$R^{11} = C_{16}H_{33}-$  [Formula 21]

$R^{12} = -(CH_2)_{11}-$ $R^{13} = H$ $R^{14} = HO-(\overset{CH_3}{\underset{|}{CH}}CH_2O)_{\bar{n}}-(CH_2)_{14}-$   $\bar{n} = 5$ (mean)

(1) Synthesis of compound (iv-j) [compound represented by the general formula (iv) in the reaction scheme of the above Formula 10 wherein $R^{14}$ is represented by the following Formula 22]:

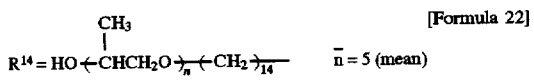

[Formula 22]

$\overline{n} = 5$ (mean)

10.0 g (33.9 mmol) of isopropyl 15-hydroxyentadecanoate, 25 ml of dimethylformamide and 0.4 g (10 mmol) of 60% sodium hydride were introduced into a 200-ml flask provided with a stirrer, a dropping funnel and a cooling tube and 19.7 g (339 mmol) of propylene oxide was added thereto, followed by stirring at 100° C. for 18 hours. After the completion of the reaction, 8 g of a 50% aqueous solution of sodium hydroxide and 80 ml of ethanol were added thereto and the resulting mixture was stirred at 60° C. for 1 hour. After cooling to room temperature, water was added to the reaction mixture. After washing with hexane and acidifying with 3N hydrochloric acid, the reaction mixture was extracted with isopropyl ether and concentrated under reduced pressure. Thus 17.0 g of a crude product of the title compound (iv-j) was obtained (crude yield: 92%).

(2) Synthesis of amide derivative (II-j):

The procedure of Example 7 was repeated except that the compound (iv-a) and the compound (iii-a) employed in Example 7 (4) to (5) were replaced respectively by the compound (iv-j) obtained above and methyl 12-aminododecanoate (iii-b). Thus the target amide derivative (II-j) was obtained.

The physical -properties of the amide derivative (II-j) thus obtained are as follows:

A pale yellow solid.

m.p.: 74.2°–80.3° C.

IR (neat, cm$^{-1}$): 3320, 2920, 2852, 1614, 1464, 1102

$^1$H-NMR (CDCl$_3$, δ): 0.79–1.00 (m, 3H), 1.00–1.24 (m, about 15H), 1.24–1.82 (m, 70H), 1.87–2.04 (m, 2H), 2.15 (t, J=7.4Hz, 2H), 2.32–2.48 (m, 2H), 3.11–4.39 (m, about 31H), 5.56 (bs, 1H)

EXAMPLE 14

The dermatologic preparations of the present invention comprising 10% of each of the amide derivatives of the present invention listed in the following Table 4 and 90% of sqalane were prepared. Then the transepidermal water loss and percutaneous absorption of each dermatologic preparation were evaluated in the same methods as those employed in Example 5. For comparison, a comparative dermatologic preparation comprising squalane alone was also evaluated. Table 4 summarizes the results.

TABLE 4

|  | Amide derivative | Transepidermal water loss | Percutaneous absorption |
|---|---|---|---|
| Product of Invention | Compound of Ex. 7 | 11.5 ± 1.79 | 568 ± 133 |
|  | Compound of Ex. 8 | 11.2 ± 0.93 | 551 ± 212 |
|  | Compound of Ex. 9 | 22.0 ± 1.85 | 1825 ± 1110 |
|  | Compound of Ex. 10 | 23.6 ± 2.02 | 1513 ± 832 |
|  | Compound of Ex. 11 | 12.5 ± 0.89 | 912 ± 351 |
|  | Compound of Ex. 12 | 15.6 ± 1.56 | 1016 ± 389 |
|  | Compound of Ex. 13 | 21.9 ± 1.95 | 715 ± 450 |
| Comparison | squalane alone | 28.6 ± 3.40 | 2985 ± 1428 |

As the results given in the above Table 4 clearly show, each of the invention products containing the amide derivative of the present invention significantly suppressed both of the transepidermal water loss and percutaneous absorption, compared with the comparative product comprising squalane alone.

What is claimed is:

1. An amide derivative represented by the following general formula (I):

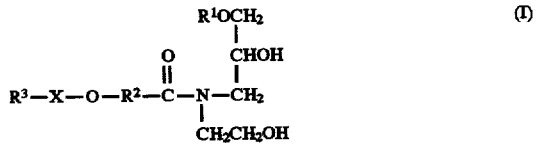

(I)

wherein $R^1$ represents a straight-chain or branched, saturated or unsaturated hydrocarbon group carrying 10 to 40 carbon atoms; $R^2$ represents a straight-chain or branched, saturated or unsaturated hydrocarbon group carrying 3 to 39 carbon atoms; $R^3$ represents a group containing at least one group represented by the formula:

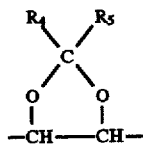

wherein $R^4$ and $R^5$ each represents a hydrogen atom or a straight-chain or branched or cyclic, saturated or unsaturated hydrocarbon group, or $R^4$ and $R^5$ may form a hydrocarbon group together; and X represents

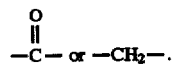

* * * * *